United States Patent
Okita et al.

(10) Patent No.: US 10,156,506 B2
(45) Date of Patent: Dec. 18, 2018

(54) RESIDUAL STRESS ESTIMATION METHOD AND RESIDUAL STRESS ESTIMATION DEVICE

(71) Applicant: KOBE STEEL, LTD., Hyogo (JP)

(72) Inventors: Keisuke Okita, Hyogo (JP); Tomokazu Nakagawa, Tokyo (JP); Mariko Yamada, Hyogo (JP)

(73) Assignee: Kobe Steel, Ltd., Hyogo (JP)

( * ) Notice: Subject to any disclaimer, the term of this patent is extended or adjusted under 35 U.S.C. 154(b) by 0 days.

(21) Appl. No.: 15/554,025

(22) PCT Filed: Feb. 22, 2016

(86) PCT No.: PCT/JP2016/055065
§ 371 (c)(1),
(2) Date: Aug. 28, 2017

(87) PCT Pub. No.: WO2016/140093
PCT Pub. Date: Sep. 9, 2016

(65) Prior Publication Data
US 2018/0067024 A1 Mar. 8, 2018

(30) Foreign Application Priority Data
Mar. 5, 2015 (JP) .................................. 2015-043083

(51) Int. Cl.
*G01N 3/08* (2006.01)
*G01L 1/00* (2006.01)

(52) U.S. Cl.
CPC .................. *G01N 3/08* (2013.01); *G01L 1/00* (2013.01); *G01N 2203/0075* (2013.01); *G01N 2203/0218* (2013.01); *G01N 2203/0246* (2013.01)

(58) Field of Classification Search
CPC ... G01N 2203/0075; G01N 2203/0218; G01N 2203/0246; G01N 3/08; G01L 1/00
See application file for complete search history.

(56) References Cited

U.S. PATENT DOCUMENTS

2003/0222871 A1* 12/2003 Brombolich ........ G06F 17/5018
345/427
2016/0273979 A1* 9/2016 Yamada ................ G01L 5/0047

FOREIGN PATENT DOCUMENTS

| EP | 2 363 819 A1 | 9/2011 |
| JP | H05-223661 A | 8/1993 |

(Continued)

OTHER PUBLICATIONS

International Search Report issued in PCT/JP2016/055065; dated May 17, 2016.

(Continued)

*Primary Examiner* — Francis C Gray
(74) *Attorney, Agent, or Firm* — Studebaker & Brackett PC

(57) ABSTRACT

Provided is a residual stress estimation method and a residual stress estimation device which are capable of setting an appropriate analysis range without depending on a user's experience. The residual stress estimation device displays analysis results in which strain generated in a structure is analyzed. A user determines a position and a size of an analysis range based on the analysis results, and inputs the determined position and size of the analysis range and a measured value of residual stress of a cut piece of the structure at a measurement point to the residual stress estimation device. The residual stress estimation device estimates distribution of inherent strain in the analysis range to approximate the inherent strain distribution obtained from the input measured value of the residual stress of the cut (Continued)

piece, thereby estimating the residual stress of the structure based on the inherent strain.

9 Claims, 12 Drawing Sheets

(56) References Cited

FOREIGN PATENT DOCUMENTS

| | | | | |
|---|---|---|---|---|
| JP | 2003-121273 A | | 4/2003 | |
| JP | 2003121273 A | * | 4/2003 | |
| JP | 2005-181172 A | | 7/2005 | |
| JP | 2013036902 A | * | 2/2013 | |
| JP | 2015222207 A | * | 12/2015 | |
| WO | WO 2007028360 A1 | * | 3/2007 | ............ G01H 9/002 |

OTHER PUBLICATIONS

Written Opinion issued in PCT/JP2016/055065; dated May 17, 2016.

The European search report issued by the European Patent Office dated Oct. 2, 2018, which corresponds to European Patent Application No. 16758787.2-1001 and is related to U.S. Appl. No. 15/554,025.

\* cited by examiner

RESIDUAL STRESS ESTIMATION METHOD AND RESIDUAL STRESS ESTIMATION DEVICE

TECHNICAL FIELD

The present invention relates to a residual stress estimation method and a residual stress estimation device for estimating the residual stress of a structure based on an inherent strain method.

BACKGROUND ART

Residual stress generated in a structure causes damage such as fatigue cracks in some cases and it is important to accurately grasp the distribution of the residual stress in the structure. As a method of estimating the residual stress of a structure, there has been known a method using an inherent strain method (for example, refer to Patent Documents 1 and 2).

In a method of estimating residual stress based on the inherent strain method of the related art, two kinds of cut pieces are cut out from a structure, the elastic strain or residual stress of each cut piece is measured, and the measured value of the elastic strain or residual stress of each cut piece is applied to inverse analysis process based on a finite element method. A user inputs an assumed range in which the inherent strain is generated in the cut piece to an analysis device that performs inverse analysis process, as an analysis range. The analysis device approximates inherent strain distribution with a least squares method using a distribution function defined in the analysis range, determines the inherent strain distribution in the analysis range, and calculates the residual stress of the structure from the obtained inherent strain distribution.

CITATION LIST

Patent Reference

Patent Document 1: JP-A-2005-181172
Patent Document 2: JP-A-2003-121273

SUMMARY OF THE INVENTION

Problems that the Invention is to Solve

The estimation precision of the residual stress is greatly affected by the set analysis range. Thus, it is important to set the analysis range appropriately. However, conventionally, the user has set the analysis range through trial and error based on experience, and the appropriate analysis range cannot always be set.

The present invention is made in consideration of the above circumstances and a primary object thereof is to provide a residual stress estimation method and a residual stress estimation device that can solve the above problems.

Means for Solving the Problems

In order to resolve the problems described above, according to an aspect of the invention, a residual stress estimation method includes steps of: analyzing strain generated in a structure and displaying analysis results, without using a measured value of the structure; acquiring conditions concerning an analysis range, which is set based on the analysis results, for estimating residual stress; acquiring the measured value for the residual stress of the structure; and estimating distribution of inherent strain in the analysis range using the measured value, based on the acquired conditions concerning the analysis range, to approximate the inherent strain of the structure in the analysis range.

In the residual stress estimation method, the step of acquiring conditions concerning the analysis range may include acquiring a position and a size of the analysis range as the conditions concerning the analysis range, and the step of estimating the distribution of the inherent strain may include estimating the distribution of the inherent strain in the analysis range specified by the acquired position and size.

In the residual stress estimation method, the step of acquiring the measured value may include acquiring elastic strain and residual stress measured at the measurement point in the analysis range specified by the acquired position and size, as the measured value.

In the residual stress estimation method, the step of acquiring conditions concerning the analysis range may include acquiring information defining a plurality of divided regions that divide the analysis range as the conditions concerning the analysis range, and the step of estimating the distribution of the inherent strain may include determining a parameter of a distribution function to approximate the distribution function, which is a set of a plurality of piecewise functions defined for each of the plurality of divided regions defined by the acquired information, to the inherent strain distribution of the analysis range based on the measured value.

In the residual stress estimation method, the step of estimating the distribution of inherent strain may include determining the parameter of the distribution function so that each piecewise function is made continuous at a boundary of each divided region.

In the residual stress estimation method, the step of estimating the distribution of inherent strain may include determining the parameter of the distribution function based on spline interpolation so that a gradient of each piecewise function is made continuous at a boundary of each divided region.

In the residual stress estimation method, the step of displaying the analysis results may include performing elasto-plastic analysis on a three-dimensional model simulating the structure by a finite element method.

In the residual stress estimation method, the step of displaying the analysis results may include analyzing stress generated by processing of the structure based on Hertz contact theory.

In addition, according to another aspect of the invention, a residual stress estimation device includes: an analysis unit for analyzing strain generated in a structure, without using a measured value of the structure; a display unit for displaying analysis results by the analysis unit; an input unit for receiving an input of conditions concerning an analysis range, which is set based on the analysis results, for estimating residual stress and a measured value for the residual stress of the structure; an estimation unit for estimating distribution of inherent strain in the analysis range using the measured value, based on the conditions concerning the analysis range received by the input unit, to approximate the inherent strain of the structure in the analysis range; and a display unit for displaying the estimation results of the residual stress based on the distribution of the inherent strain estimated by the estimation unit.

Advantages of the Invention

According to the present invention, it is possible to set an appropriate analysis range without depending on a user's experience.

MODES FOR CARRYING OUT THE INVENTION

Hereinafter, preferred embodiments of the present invention will be described with reference to the drawings.

First Embodiment

A residual stress estimation device according to a first embodiment of the present invention is intended to estimate residual stress of a structure based on an inherent strain method for an analysis range set by a user based on an analysis solution obtained by analyzing strain generated in the structure, without using a measured value of the structure.

[Configuration of Residual Stress Estimation Device]

Figure 1:
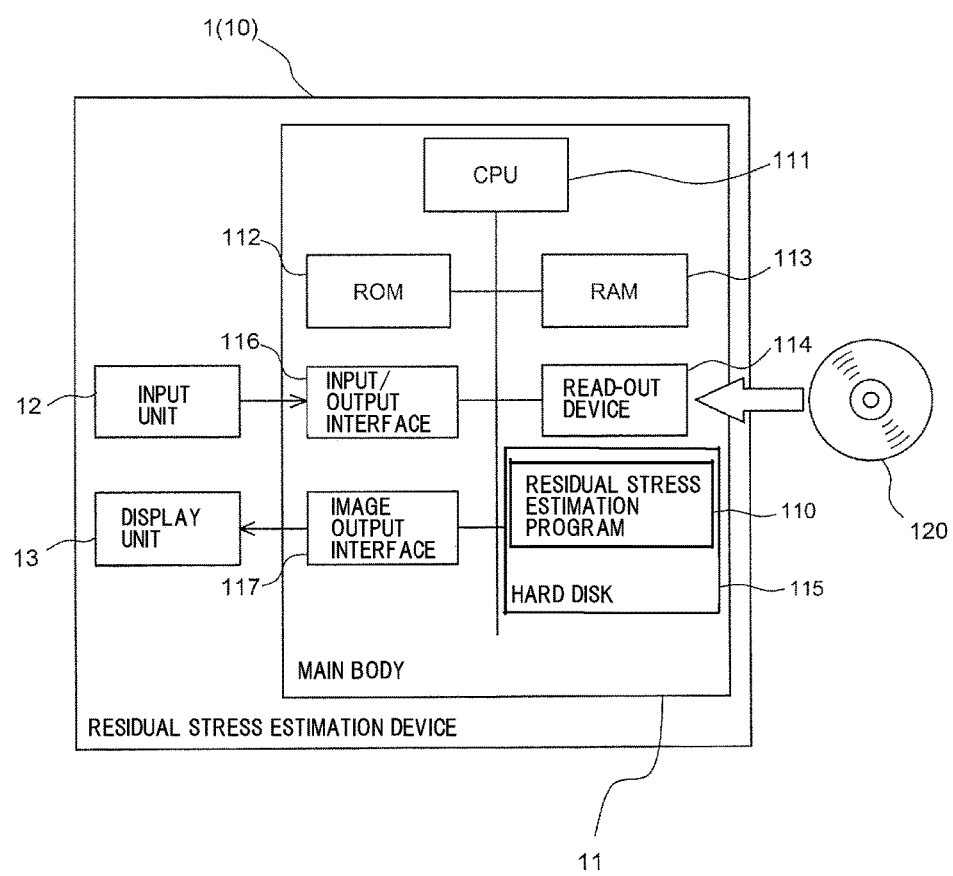
FIG. 1 is a block diagram illustrating a configuration of an embodiment of a residual stress estimation device according to the present invention.

A residual stress estimation device 1 is realized by a computer 10. As shown in FIG. 1, the computer 10 includes a main body 11, an input unit 12, and a display unit 13. The main body 11 includes a CPU 111, a ROM 112, a RAM 113, a hard disk 115, a read-out device 114, an input/output interface 116, and an image output interface 117, and the CPU 111, the ROM 112, the RAM 113, the hard disk 115, the read-out device 114, the input/output interface 116, and the image output interface 117 are connected by a bus.

The CPU 111 may execute a computer program loaded on the RAM 113. A residual stress estimation program 110 which is a computer program for residual stress estimation is executed by the CPU 111 and thus the computer 10 functions as the residual stress estimation device 1. The residual stress estimation program 110 is an inverse analysis process program based on a finite element method, and makes it possible to estimate a distribution state of inherent strain in the structure.

The ROM 112 is configured by a mask ROM, a PROM, an EPROM, an EEPROM or the like and is recorded with the computer program to be executed by the CPU 111 and the data used for the same.

The RAM 113 is configured by a SRAM, a DRAM, or the like. The RAM 113 is used to read out the residual stress estimation program 110 recorded in the hard disk 115. When the CPU 111 executes the computer program, the RAM is used as a work region of the CPU 111.

The hard disk 115 is installed with various computer programs to be executed by the CPU 111 such as the operating system, the application program, and the like, and the data used for the execution of an associated computer program. The residual stress estimation program 110 is also installed in this hard disk 115.

The hard disk 115 is installed with an operating system such as Windows (registered trademark) manufactured and sold by US Microsoft Co., for example. In the following description, the residual stress estimation program 110 according to this embodiment is assumed to operate on the operating system.

The read-out device 114 is configured by a flexible disk drive, a CD-ROM drive, a DVD-ROM drive, or the like, and can read out the computer program or the data recorded in a portable recording medium 120. The residual stress estimation program 110 is stored in the portable recording medium 120 to cause the computer to function as the residual stress estimation device. The computer 10 may read out the residual stress estimation program 110 from the portable recording medium 120 and install the residual stress estimation program 110 in the hard disk 115.

The input/output interface 116 is configured by, for example, a serial interface such as an USB, an IEEE 1394, or an RS-232C, or the like, a parallel interface such as a SCSI, an IDE, an IEEE 1284, or the like, and an analog interface including a D/A converter, an A/D converter, and the like. The input unit 12 including a keyboard and a mouse is connected to the input/output interface 116, and a user may input data into the computer 10 by using the input unit 12.

The image output interface 117 is connected to the display unit 13 configured by an LCD, a CRT, or the like, and a video signal according to the image data sent from the CPU 111 is output to the display unit 13. The display unit 13 displays an image (screen) according to the input video signal.

[Principle for Residual Stress Estimation Based on Inherent Strain Method]

(1) Calculation of Residual Stress Using Inherent Strain

When inherent strain is so, residual stress a is expressed by the following expression.

$$\sigma = D(\varepsilon - \varepsilon_0) \quad (1)$$

D represents an elastic coefficient matrix and $\varepsilon$ represents all strain satisfying the relation of the following expression.

[Equation 1]

$$\int B^T \sigma dV = \int B^T D(\varepsilon - \varepsilon_0) dV = 0 \quad (2)$$

Herein, $\int dV$ represents a volume integral in the analysis region and B represents a coefficient matrix for relating a node displacement u and c.

$$\varepsilon = Bu \quad (3)$$

In a case where the inherent strain is known, residual stress is obtained as follows.

The following expressions are given from Equations (2) and (3).

[Equation 2]

$$Ku = P \quad (4)$$

where, $$K = \int B^T DB dV \quad (5)$$

$$P = \int B^T D\varepsilon_0 dV \quad (6)$$

K represents a rigidity matrix and P represents a load vector generated by the inherent strain.

When u is obtained by solving Equation (4), residual stress may be obtained from Equations (3) and (1).

(2) Calculation of Inherent Strain Using Measured Residual Stress

N measured residual stress values are expressed as $\sigma_m$. Correspondingly, N calculated residual stress values obtained from the inherent strain are expressed as $\sigma_c$, and a residue R between the calculated residual stress and the measured residual stress is defined by the following expression.

[Equation 3]

$$R = (\sigma_m - \sigma_c)^T (\sigma_m - \sigma_c) \quad (7)$$

The inherent strain at a certain point is expressed as the following linear function by M distribution function parameters a.

[Equation 4]

$$\varepsilon_0 = Ma \quad (8)$$

where M represents a coordinate function and the coordinates may not be linear.

When the inherent strain is determined by Equation (8), the measured residual stress is obtained by the method of (1) above and as a result, a linear relation equation is obtained as follows.

[Equation 5]

$$\sigma_c = Ha \quad (9)$$

where H represents a coefficient matrix and the component thereof may be obtained by obtaining residual stress by giving a unit value to each component of a.

When Equation (9) is substituted for Equation (7) and a is determined such that R is the minimum, an inherent strain distribution in which an error between the measured residual stress and the calculated residual stress at the measurement point is the minimum is determined.

[Operation of Residual Stress Estimation Device]

Hereinafter, the operation of the residual stress estimation device 1 according to the embodiment will be described.

The residual stress estimation device 1 performs residual stress estimation processing as described below to estimate the residual stress of the structure.

Figure 2:
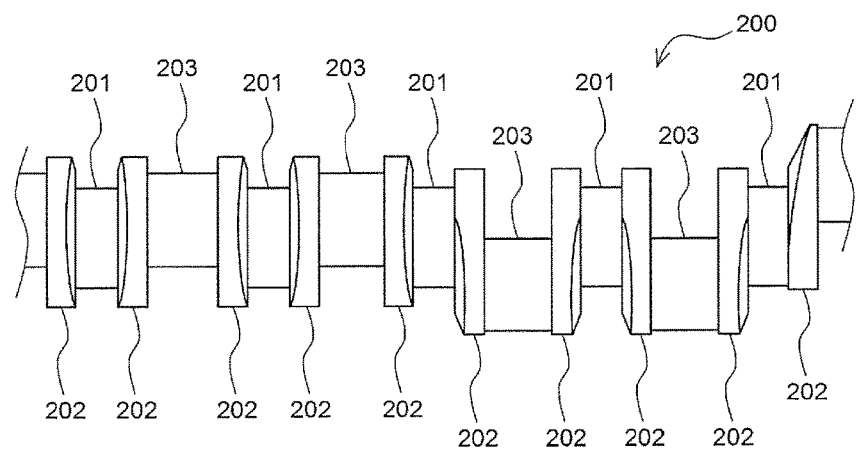
FIG. 2 is a side view illustrating a configuration of a crank shaft.

Herein, a crank shaft will be described as an example of the structure. As shown in FIG. 2, a crank shaft 200 is configured such that a journal shaft 201 and a pin shaft 203 are connected by a crank arm 202. In the connection place of the journal shaft 201 and the crank arm 202 and the connection place of the pin shaft 203 and the crank arm 202, great stress is easily generated in use. When tension residual stress is generated in these connection places, damage such as fatigue cracks may be caused. In order to improve fatigue life, plastic working such as roll processing or shot peening is performed on the connection places and compressive residual stress is introduced.

Figure 3:
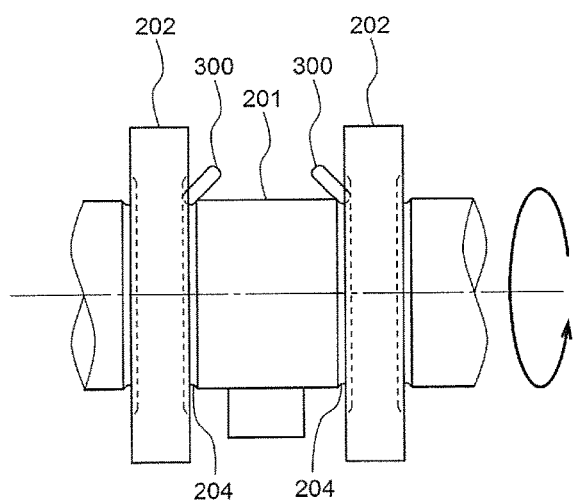
FIG. 3 is an enlarged side view illustrating plastic working for the crank shaft.

FIG. 3 is a view illustrating plastic working with respect to the crank shaft. In FIG. 3, a case of roll processing is illustrated. In the rolling processing, in a state in which a roll 300 is pressed against the connection place of the journal shaft 201 (or the pin shaft 203) and the crank arm 202, the journal shaft 201 is rotated. Thus, in the connection place, a fillet 204 is formed and compressive residual stress is applied such that the residual stress is distributed in the circumferential direction of the journal shaft 201.

Figure 4:
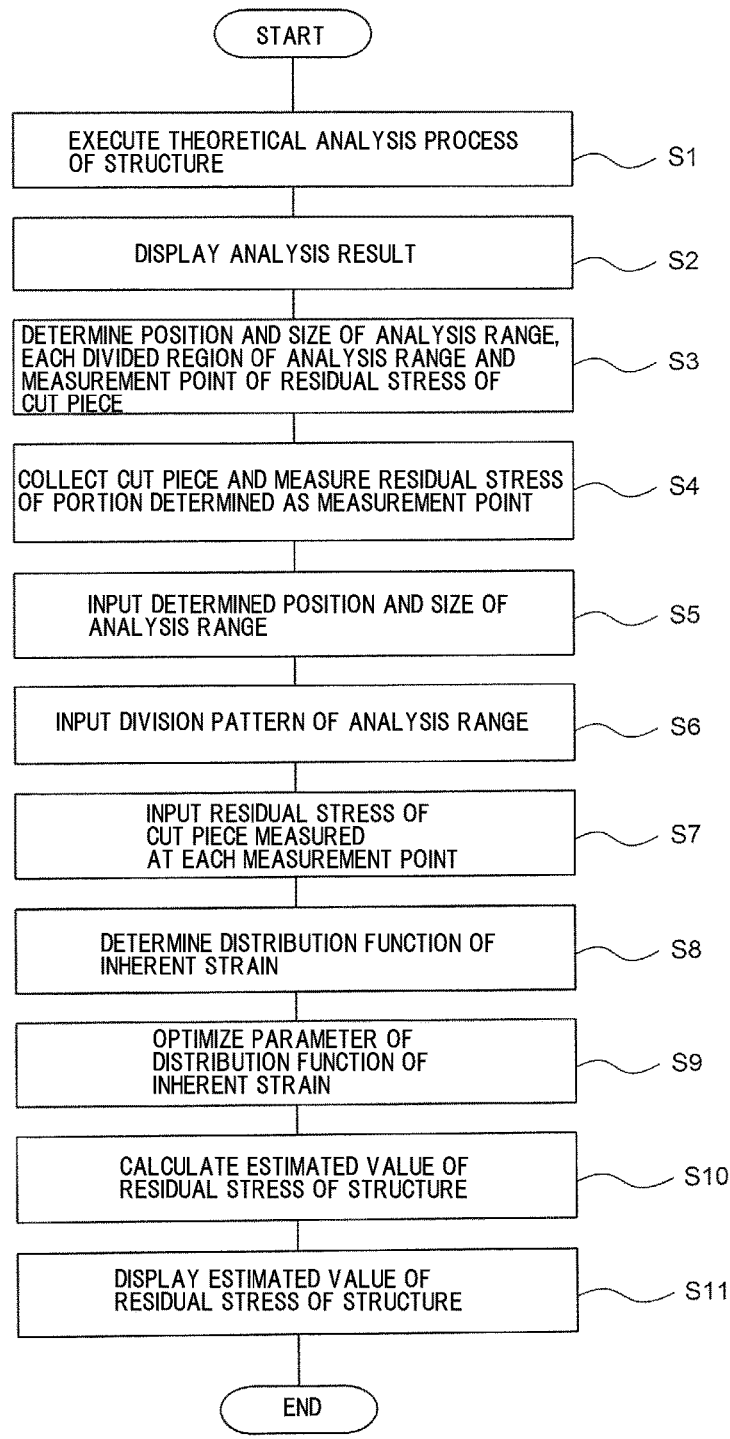
FIG. 4 is a flow chart illustrating the procedure of the embodiment of a residual stress estimation method according to the present invention.

As described above, the residual stress of the structure which is subjected to plastic working is estimated using the residual stress estimation device 1. FIG. 4 is a flow chart illustrating the procedure of a residual stress estimation method according to the embodiment.

First, the CPU 111 executes a theoretical analysis process of the structure (step S1).

The theoretical analysis process is a process of analyzing the strain in the structure without using the measured value of the structure. More specifically, an elasto-plastic analysis based on the finite element method is used. In the theoretical analysis process, the CPU 111 performs a processing simulation for a three-dimensional model of the structure under the same processing conditions as the real conditions, and analyzes the distribution state of the strain in the structure.

Figure 5A:
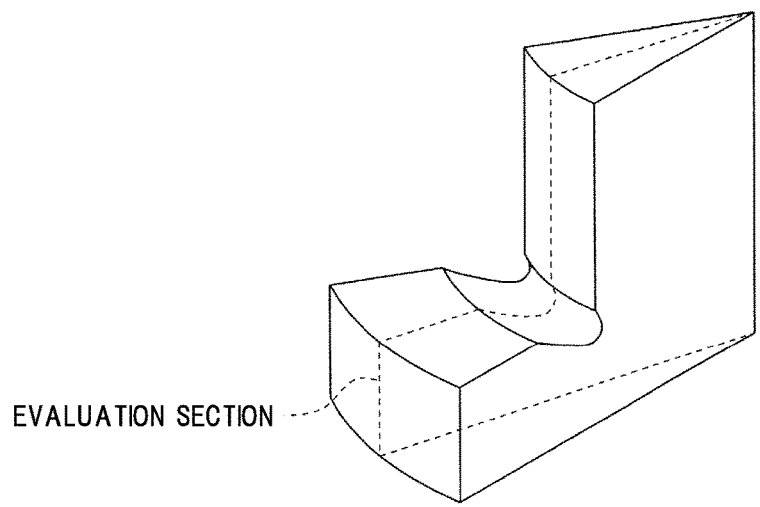
FIG. 5A is a perspective view illustrating an analysis model.
Figure 5B:
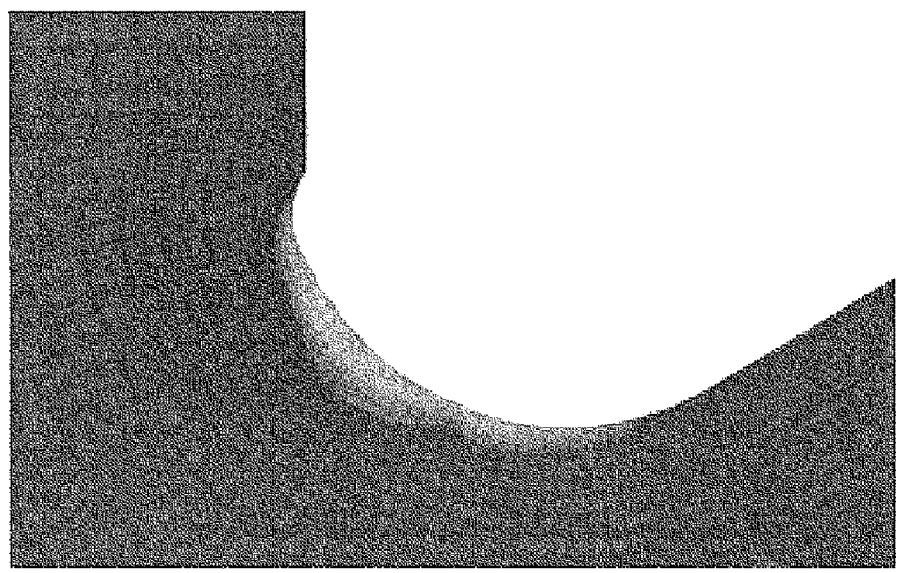
FIG. 5B is a view illustrating analysis results of a strain distribution state in the analysis model illustrated in FIG. 5A.

An example of a three-dimensional model (analysis model) will be described. When the roll processing conditions of a real machine are simulated and a roll is rotated while considering a contact with the fillet, the residual stress was analyzed in a fillet portion of the crank shaft. FIG. 5A is a perspective view illustrating an analysis model. An axially symmetric shape is considered, the analysis model is modeled at 30° in the circumferential direction, and symmetric conditions in the circumferential direction are applied to a circumferential end face. FIG. 5B is a view illustrating the analysis results of the strain distribution state in the analysis model illustrated in FIG. 5A. In FIG. 5B, a center plane (section at the position of 15°) in the circumferential direction of the analysis model is taken as an evaluation section, and the analysis results of the strain in this evaluation section are shown.

Next, the CPU 111 displays the analysis results of the theoretical analysis process onto the display unit 13 (step S2). In the process of step S2, the CPU 111 causes the display unit 13 to display a screen through which a user may understand the distribution state of strain in the three-dimensional model. Examples thereof include a graphic display that color-classifies the distribution state of the strain in the section of the three-dimensional model depending on an intensity level of the strain, and the like.

In step S2, it is preferable to display a contour line for each strain intensity level. Thus, it is easy for a user to determine the divided region of the analysis range that will be described below.

A user determines conditions relating to the analysis range in which the residual stress is estimated, that is, the position and size of the analysis range, each divided region of the analysis range, and a measurement point of residual stress, with reference to the analysis results screen of the theoretical analysis process (step S3).

In the theoretical analysis process, it is not possible to accurately estimate the strain, but it is possible to approximately accurately estimate a strain generating region. Therefore, a user may check the distribution state of the strain by the analysis result screen of the theoretical analysis process and then determine the position and size of the analysis range suitable for estimating the residual stress.

Figure 6:
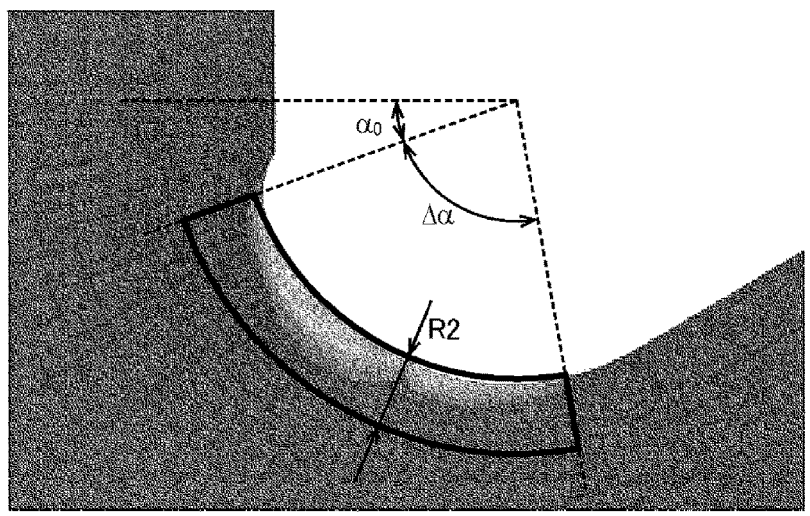
FIG. 6 is a view illustrating the determination of a position and a size of an analysis range.

The determination of the position and size of the analysis range will be described in detail with reference to FIG. 6. FIG. 6 illustrates the intensity level of strain obtained by the theoretical analysis process, by gray shade. A user may easily obtain an appropriate analysis range by determining the position and size of the analysis range to surround a region in which the strain is generated.

As will be described later, the inherent strain distribution is estimated using a distribution function. Conventionally, in the distribution function, a series expanded expression is used throughout an entire analysis range. That is, one distribution function is defined for one analysis range. Thus, often, the conventional distribution function may not deal with the bias of the inherent strain distribution in the analysis range, and may not accurately reproduce a real inherent strain distribution. Therefore, the residual stress estimation device 1 divides the analysis range into a plurality of divided regions, and defines the distribution function as a set of a piecewise function defined as the divided region. If a small divided region is set in a portion where a change in inherent strain is steep and a large divided region is set in a portion where a change in inherent strain is gentle, it is possible to accurately match the distribution function with the distribution shape of the inherent strain in each divided region. Thus, a user may check the strain distribution state by the analysis result screen of the theoretical analysis process, and may appropriately determine each divided region in the analysis range.

Figure 7:
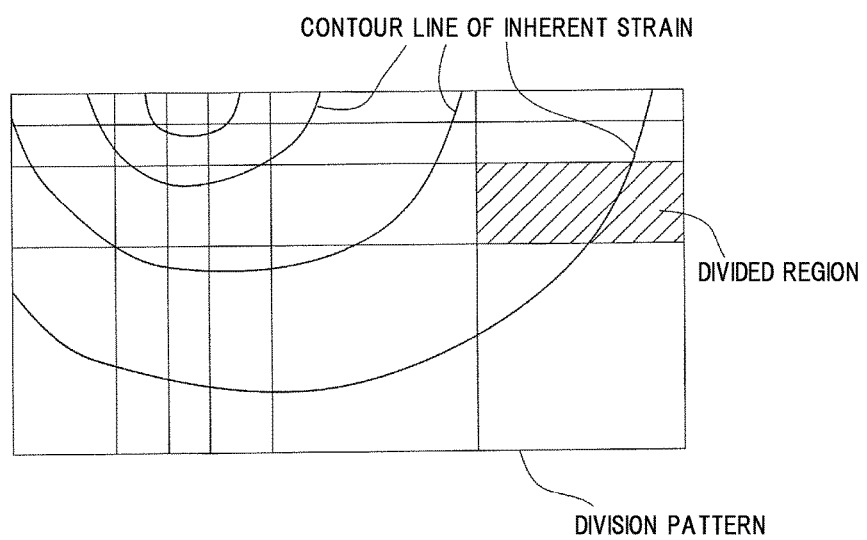
FIG. 7 is a view illustrating the determination of a divided region in the analysis range.

The divided region in the analysis range will be described in detail with reference to FIG. 7. In FIG. 7, the contour line is marked for each intensity level of strain obtained by the theoretical analysis process. A change in strain is steep in a portion where an interval between contour lines is narrow, and a change in strain is gentle in a portion where an interval between contour lines is wide. A user divides a region according to the interval between the contour lines so that the divided region is decreased in a portion where the interval between the contour lines is narrow and the divided region is increased in a portion where the interval between the contour lines is wide, thus making it easy to obtain an appropriate divided region.

Here, it is preferable for a user to determine the same number of measurement point for each divided region. Thus, it is possible to cope with a steep change in inherent strain in the small divided region and to cope with a gentle change in inherent strain in the large divided region.

The residual stress of the structure is estimated based on the residual stress (or elastic strain) of the measured cut piece. Thus, the location of the measurement point significantly affects the estimation precision of the residual stress of the structure. If a portion where the value of the inherent strain is high, a portion where the distribution of the inherent strain is steeply changed or the like is set as the measurement point, it is possible to accurately estimate the residual stress. Therefore, a user may check the distribution state of the inherent strain by the analysis result screen of the theoretical analysis process, and determine a portion suitable for measuring the residual stress (or elastic strain) of the cut piece as the measurement point.

The portion where the value of the inherent strain is high, the portion where the distribution of the inherent strain is steeply changed or the like may be a portion suitable for estimating the residual stress. That is, the analysis range suitable for estimating the residual stress includes a portion suitable for measuring the residual stress (or elastic strain) of the cut piece. Therefore, the user determines the measurement point in the analysis range.

A user cuts the structure, collects a cut piece from a portion determined as the measurement point, and measures the residual stress from the cut piece (Step S4). Generally, the structure is thinly cut in one direction to collect a cut piece (T piece) and is thinly cut in a direction perpendicular to the one direction to collect a cut piece (L piece).

Here, the residual stress is a value obtained by multiplying elastic strain by a Young's modulus, and measuring elastic strain is equivalent to measuring residual stress. Accordingly, either elastic strain or residual stress may be measured from the cut piece. In the embodiment, a case of measuring the residual stress will be described.

Figure 8:
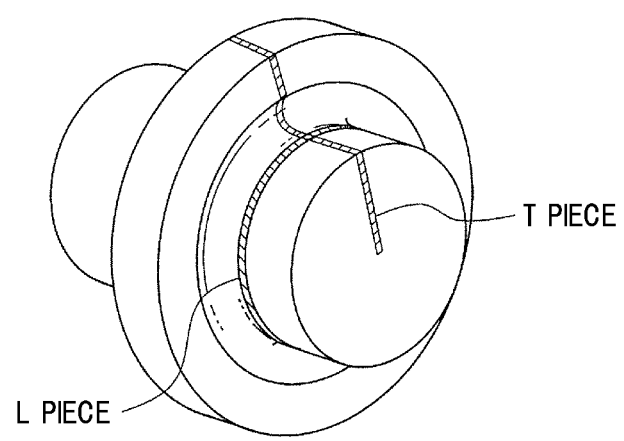
FIG. 8 is a perspective view illustrating an example of a cut piece collected from a structure.

As shown in FIG. 8, in the case of an axis-symmetric structure, such as a journal shaft or a pin shaft, to which the compressive residual stress is uniformly applied in the circumferential direction, a T piece is obtained by cutting the structure in a radial direction. If the inherent strain is uniformly distributed in the circumferential direction, even in a case where a T piece is obtained from any portion in the circumferential direction, the inherent strain does not change. Accordingly, the T piece to be collected may be only one. Accordingly, the number of T pieces to be collected can be reduced. Thus, it is possible to reduce the workload of the cutting processing and the measurement of the residual stress of the cut piece.

On the other hand, the inherent strain distribution in the shaft length direction is complicated. Accordingly, it is necessary to collect the L piece in a plurality of places in the shaft length direction.

Figure 9:
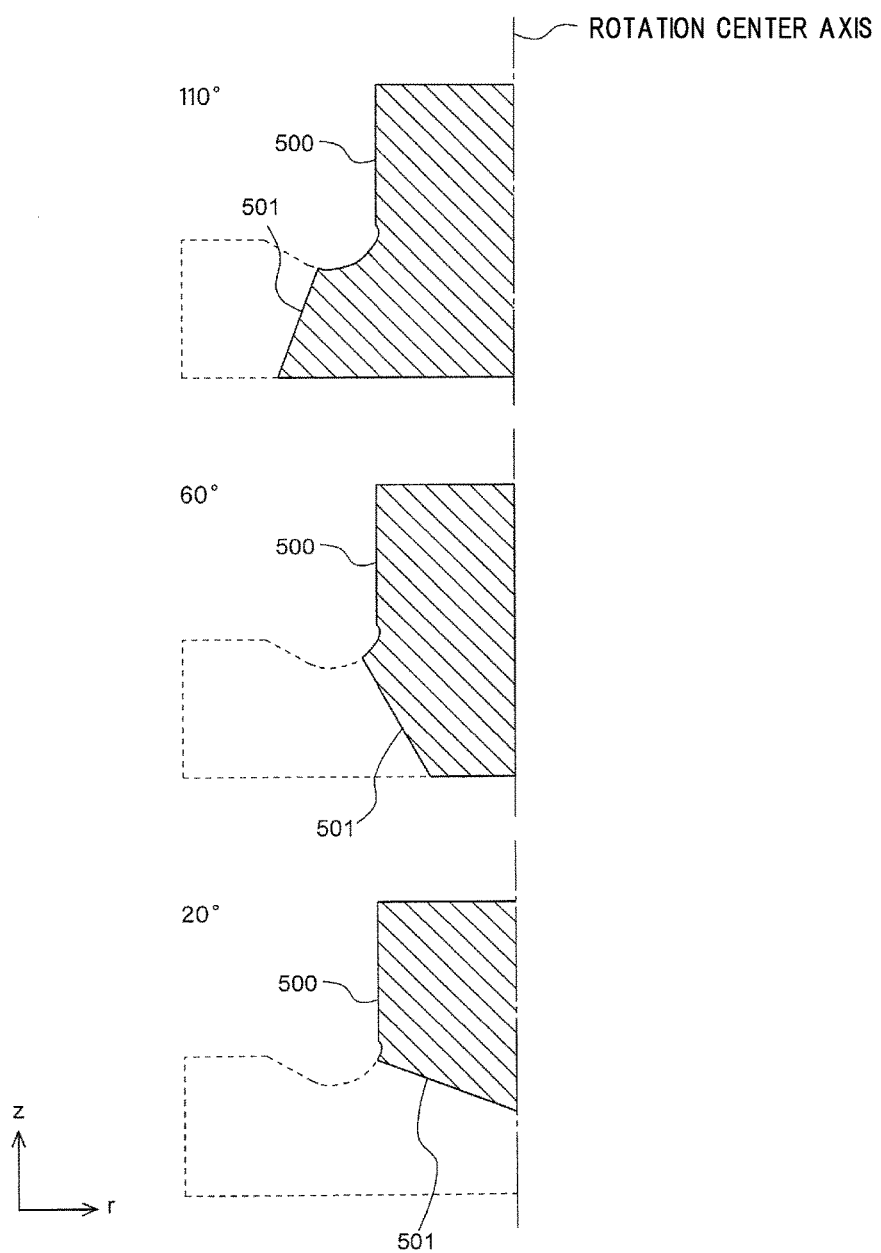
FIG. 9 is a cross-sectional view of a journal shaft for illustrating collection of a C piece.

In a case of having a bent surface like the fillet portion of the crank shaft, instead of the L piece, a conical cut piece (hereinafter, referred to as "C piece") cut in a direction normal to the bent surface may be collected. In addition, the L piece and the C piece are not collected and only the T piece may be collected. In FIG. 9, each view is a cross-sectional view when the journal shaft is cut in the rotation axis length direction. A C piece 500 is obtained by cutting the structure in a direction normal to the bent surface of the fillet, that is, in the radius direction of the arc-shaped fillet in the section. Since the journal shaft has an axis-symmetric shape, a cut face 501 of the C piece 500 conically extends around the rotation center axis of the journal shaft. Several C pieces are collected by changing the central angle of the fillet (for example, from 20° to 110° with a step of 10°).

In a case where compressive residual stress is uniformly applied to a rod-like structure long in one direction in the longitudinal direction, only one T piece can be collected in one place in the longitudinal direction.

The user directly measures the residual stress of the cut piece collected as described above with X-rays or the like. In the case of measuring the elastic strain, the user attaches a strain gauge to the cut piece and further cut the cut piece into a plurality of small pieces to measure released strain (elastic strain) of each small piece. In the measurement of the residual stress or released strain (elastic strain), a plurality of components that are different from each other are measured.

FIG. 4 is referred to again. The user inputs the position and size of the determined analysis range into the residual stress estimation device 1. The CPU 111 of the residual stress estimation device 1 receives the position and size of the analysis range input from the input unit 12 (Step S5).

Next, the user inputs a division pattern (information about division position) of the analysis range into the residual stress estimation device 1. The CPU 111 of the residual stress estimation device 1 receives the division pattern of the analysis region input from the input unit 12 (Step S6).

Next, the user inputs the measured value of the residual stress into the residual stress estimation device 1. The CPU 111 of the residual stress estimation device 1 receives the measured value input from the input unit 12 (Step S7).

Next, the CPU 111 determines the distribution function (Step S8). The distribution function is defined as a set of a plurality of piecewise functions defined for each divided region of the analysis range. For each piecewise function, a certain multi-order polynomial may be selected. However, in order to obtain estimation results that correctly reflect the distribution state of the inherent strain, the order of each piecewise function is preferably made common. Accordingly, it is possible to cope with a change in gentle inherent strain in a large divided region, while coping with a change in steep inherent strain in a small divided region. Further, as will be described later, the order of each piecewise function is made common even in the case of performing spline interpolation.

The CPU 111 may automatically select the distribution function or the user may designate a distribution function using the input unit 12. In the residual stress estimation device 1, the distribution function may be set in advance.

Next, the CPU 111 optimizes the parameters of the distribution function (Step S913). Hereinafter, the processing of Step S9 will be described in detail.

The CPU 111 first determines H in Expression (9). The procedure thereof is as follows.

(a) $a=[1, 0, 0, \ldots, 0]^T$ is set and $\varepsilon_0=Ma$ is obtained.
(b) Expression (4) is solved and u is obtained.
(c) ε is obtained by Expression (3).
(d) σ is obtained by Expression (1).
(e) N values corresponding to the residual stress measurement point are extracted from the components of a and the extracted values are set to a first column of H.
(f) $a=[0, 1, 0, \ldots, 0]^T$ is set and a second column of H is also obtained in the same procedure of (b) to (f).

Next, the CPU 111 determines such that R of Expression (7) is the minimum. Accordingly, the distribution function parameters are optimized.

In the processing of Step S9, the CPU 111 preferably determines the parameters of the distribution function so that the gradient of each piecewise function is continuous by the spline interpolation. Thus, the inherent strain may be smoothly continued at a boundary of the divided region, and an estimated value of the inherent strain may be obtained without impairing physical properties.

Further, the CPU 111 calculates an estimated value of the residual stress (Step S10).

In the processing of Step S10, first, the CPU 111 obtains the inherent strain of a certain point by Expression (8). Further, the CPU 111 obtains u by solving Expression (4) and the obtained u is applied to Expression (3) to obtain ε. Then, the obtained s is applied to Expression (1) to obtain σ.

Next, the CPU 111 displays the estimated value of the obtained residual stress on the display unit 13 (Step S11).

After Step S11, the CPU 111 ends the processing.

Second Embodiment

The residual stress estimation device according to this embodiment analyzes stress generated by the processing of the structure based on the Hertz contact theory, in the theoretical analysis process (Step S1).

Since the remaining configuration of the residual stress estimation device according to the present embodiment is the same as the configuration of the residual stress estimation device 1 according to the first embodiment, a detailed description thereof will not be repeated.

The theoretical analysis process in the residual stress estimation device according to this embodiment will be described. The Hertz contact theory is used to analyze stress in point contact or line contact with two elastic bodies. Here, a case where the Hertz contact theory is applied to roll processing of the crank shaft will be described.

The roll processing is a type of plastic working. Although it is not possible to calculate the stress when plastic strain occurs by the Hertz contact theory, it is possible to estimate the plastic strain, that is, a region where the plastic strain occurs.

Figure 10:
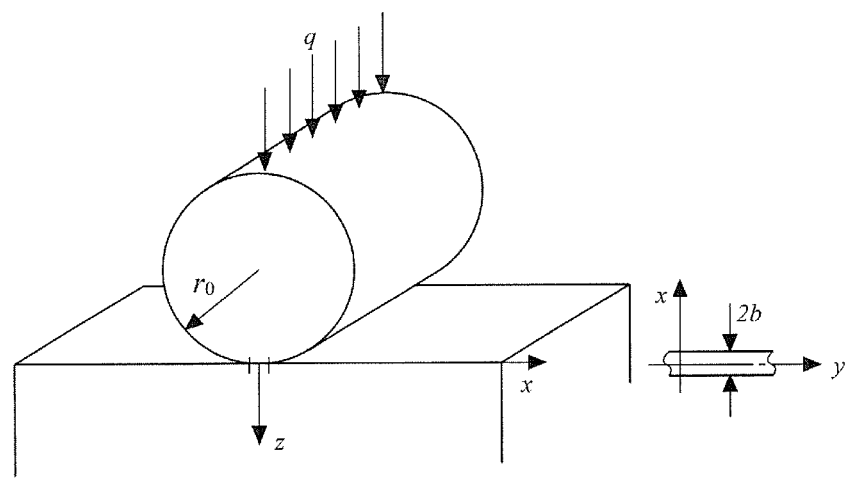
FIG. 10 is a view illustrating an example of a contact problem for illustrating Hertz contact theory.
Figure 11:
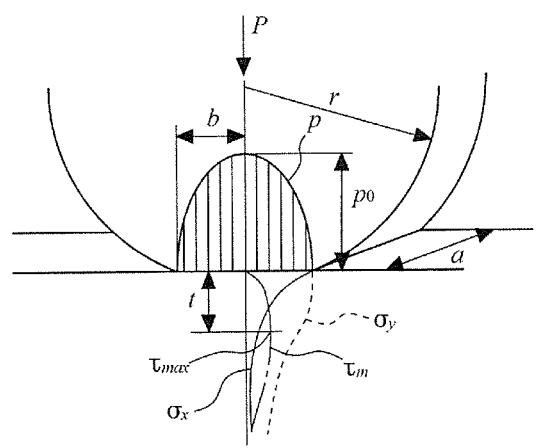
FIG. 11 is a view illustrating a stress distribution assumed when a cylinder and a flat plate illustrated in FIG. 10 are in contact with each other.

A problem of contact between the cylinder and the flat plate as illustrated in FIG. 10 is considered. FIG. 11 is a view illustrating a stress distribution assumed when the cylinder and the flat plate illustrated in FIG. 10 are in contact with each other.

The distribution of each stress component in a depth direction just under the contact (x=0) is as shown by a hatching portion of FIG. 11, and is represented by Expressions (10) to (14).

[Equation 6]

$$(\sigma_x)_{x=0} = -p_0 \frac{b}{\sqrt{b^2+z^2}} \left[1 - \frac{2z}{b}\left(\sqrt{1+\frac{z^2}{b^2}} - \frac{z}{b}\right)\right] \quad (10)$$

$$(\sigma_y)_{x=0} = -p_0 \frac{2vb}{\sqrt{b^2+z^2}} \left[1 - \frac{z}{b}\left(\sqrt{1+\frac{z^2}{b^2}} - \frac{z}{b}\right)\right] \quad (11)$$

$$(\sigma_z)_{x=0} = -p_0 \frac{b}{\sqrt{b^2+z^2}} \quad (12)$$

$$\tau_1 = \frac{(\sigma_x - \sigma_z)_{x=0}}{2} \quad (13)$$

$$\tau_2 = \frac{1}{2}(\sigma_y - \sigma_z)_{x=0} \quad (14)$$

-continued $$b^2 = \frac{4}{\pi}r_0\left(\frac{1-v_1^2}{E_1} + \frac{1-v_2^2}{E_2}\right)q \quad (15)$$

$$p_0^2 = \frac{1}{\pi}\frac{q}{r_0}\frac{1}{\frac{1-v_1^2}{E_1} + \frac{1-v_2^2}{E_2}} \quad (16)$$

$$p = p_0\sqrt{1 - \frac{x^2}{b^2}} \quad (17)$$

Here, $E_1$ and $E_2$ are modulus of longitudinal elasticity, $v_1$ and $v_2$ are Poisson's ratio, P is concentrated load, q is line load per unit length, p is pressure on a contact surface, $p_0$ is maximum pressure generated at a center of the contact surface, $r_0$ is a radius of the cylinder, and 2b is a width of a rectangle of the contact surface. Further, p, $p_0$ and b are obtained from Expressions (15) to (17).

Here, according to the maximum shear stress theory that is Tresca's yield condition, the yield stress of uniaxial tension of a material is $\sigma_y$, and a yield starts when shear stress $\tau$ acting on the material satisfies Expression (18) (plastic strain is generated).

[Equation 7]

$$\sigma_y = 2\tau \quad (18)$$

Therefore, for the flat plate, expression (19) is obtained from expressions (10), (12), (13) and (18), and the depth z from the surface in expression (19) is a hardening depth, that is, the region in which the plastic strain (inherent strain) is generated.

[Equation 8]

$$\sigma_y = \frac{2p_0}{b}\left(z - \frac{z^2}{\sqrt{b^2 + z^2}}\right) \quad (19)$$

The analysis results obtained by the theoretical analysis process using the above-described Hertz contact theory are displayed on the display unit 13 in step S2. At this time, the strain may be displayed on a contour line for each intensity level.

Such a configuration allows a user to check the analysis results of the theoretical analysis process, thus appropriately determining the position and size of the analysis range that is the range for estimating the residual stress, each divided region of the analysis range, and the measurement point of the residual stress (or elastic strain) of the cut piece, without depending on experience.

Other Embodiments

In the above-described first and second embodiments, there has been described a configuration which is based on the analysis results of the theoretical analysis process and in which a user determines the position and size of the analysis range, each divided region of the analysis range, and the measurement point of the residual stress of the cut piece, and inputs the position and size of the analysis range, each divided region of the analysis range, and the measured value of the residual stress at the measurement point into the residual stress estimation device respectively, but the invention is not limited thereto. Based on the analysis results of the theoretical analysis process, the user may determine at least one of the position and size of the analysis range, each divided region of the analysis range, and the measurement point of the residual stress of the cut piece. When the user determines the position and size of the analysis range, the residual stress estimation device receives the position and size of the analysis range which are input thereto, and estimates the residual stress based on the inherent strain in this analysis range. When the user determines each divided region of the analysis range, the residual stress estimation device receives the division pattern of the analysis range which is input thereto, and estimates the residual stress based on the inherent strain, using the distribution function that is the set of the piecewise function defined for each divided region. When the user determines the measurement point of the residual stress, the residual stress estimation device receives the measured value of the residual stress at the determined measurement point which is input thereto, approximates the inherent strain based on the input measured value, and estimates the residual stress of the structure.

Further, in the above-described first and second embodiments, there has been described a configuration in which spline interpolation is applied to determine the parameter of the distribution function, but the invention is not limited thereto. The parameter of each piecewise function may be determined without using the spline interpolation. In this case, Lagrange interpolation may be applied to determine the parameter of each piecewise function. Accordingly, each piecewise function may be made continuous at the boundary of the divided region. Further, it is possible to define an analytic function of one multi-order polynomial or trigonometrical series in an entire analysis region and apply Lagrange interpolation to optimize the parameter of this distribution function. Likewise in the case of using Lagrange interpolation, it is possible to cope with the bias of the distribution of the inherent strain, assuming that the number of measurement points in each divided region is the same.

Further, in the above-described first and second embodiments, there has been described a configuration in which a user inputs the condition for the analysis range (the position and size of the analysis range, the divided region of the analysis range, and the measurement point of the residual stress of the cut piece) into the residual stress estimation device, but the invention is not limited thereto. The residual stress estimation device may automatically set the condition for the analysis range, based on the analysis results of the theoretical analysis process.

Further, in the above-described first and second embodiments, there has been described a configuration in which the residual stress is measured from the cut piece of the structure and the parameter of the distribution function is optimized such that a difference between the measured residual stress and the residual stress calculated by the distribution function is the minimum, but the invention is not limited thereto. A configuration in which the released strain (elastic strain) is measured from the cut piece of the structure and the parameter of the distribution function is optimized such that a difference between the measured released strain and the elastic strain calculated by the distribution function is the minimum may be adopted. In this case, the determination of the measurement point of the elastic strain is the same as the determination of the measurement point of the residual stress in the first and second embodiments.

(Evaluation Test)

The inventor(s) conducted performance evaluation tests of the residual stress estimation method described in the above embodiments. In this evaluation test, a correct answer value of the residual stress used the analysis results of the existing FEM (finite element method) analysis, conducted a numerical experiment by a residual stress estimation method (hereinafter, referred to as a "proposed method") using an analysis range that is set based on the analysis results by the theoretical analysis process, and compared the correct answer value with the numerical experiment results.

In this evaluation test, the residual stress in a pin axis of the crank shaft was estimated by the analysis model shown in FIG. 5A. The center plane (section at a position of 15°) in the circumferential direction of the analysis model was taken as the evaluation section, and the results in the evaluation section were used as the correct answer value.

In the numerical experiment, it is considered to use an inherent strain value under the same condition (position, component) as an actually measuring case. After simulating roll processing, T and C pieces were collected in the FEM analysis and strain released analysis was performed to obtain residual stress corresponding to actual measurement.

(1) Test 1

In the proposed method, when the analysis results by the theoretical analysis process shown in FIG. 6 is obtained (fillet angle=40°), the position and size of the analysis range to surround the strain generating region indicated in the analysis results were set (analysis range shown in FIG. 6). Both when the analysis range larger than the proposed method was set (hereinafter referred to as "comparative method 1") and when the analysis range smaller than the proposed method was set (hereinafter referred to as "comparative method 2"), the residual stress was estimated and compared with the results of the proposed method. In the following table, the setting conditions of the analysis range in the proposed method, comparative method 1 and comparative method 2 are shown.

TABLE 1

|  | $\alpha_0[°]$ | $\Delta\alpha[°]$ | R2[mm] |
| --- | --- | --- | --- |
| Comparative method 1 | 0 | 120 | 20 |
| Comparative method 2 | 30 | 70 | 2 |
| Proposed method | 20 | 80 | 6 |

Figure 12A:
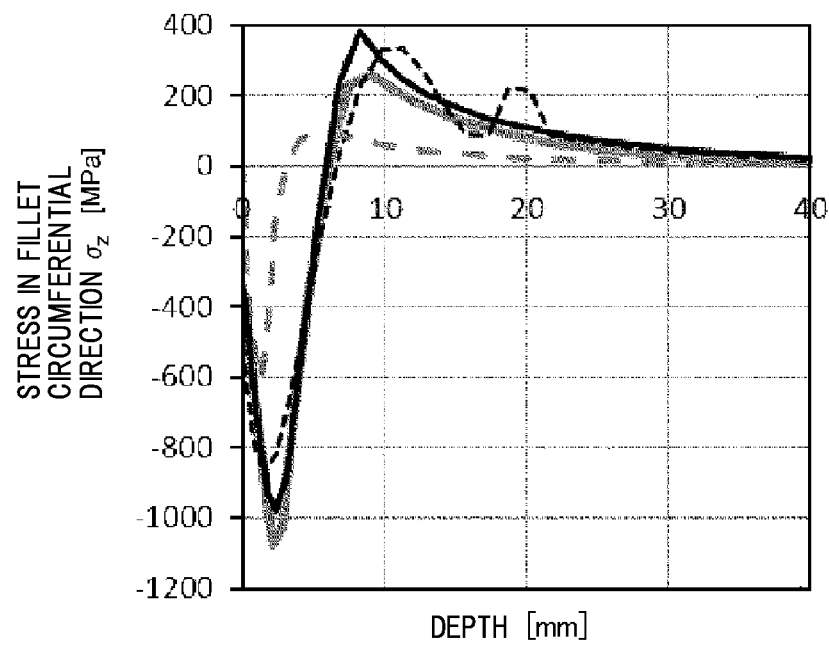
FIG. 12A is a graph illustrating estimation results of residual stress in a fillet circumferential direction in Test 1.
Figure 12B:
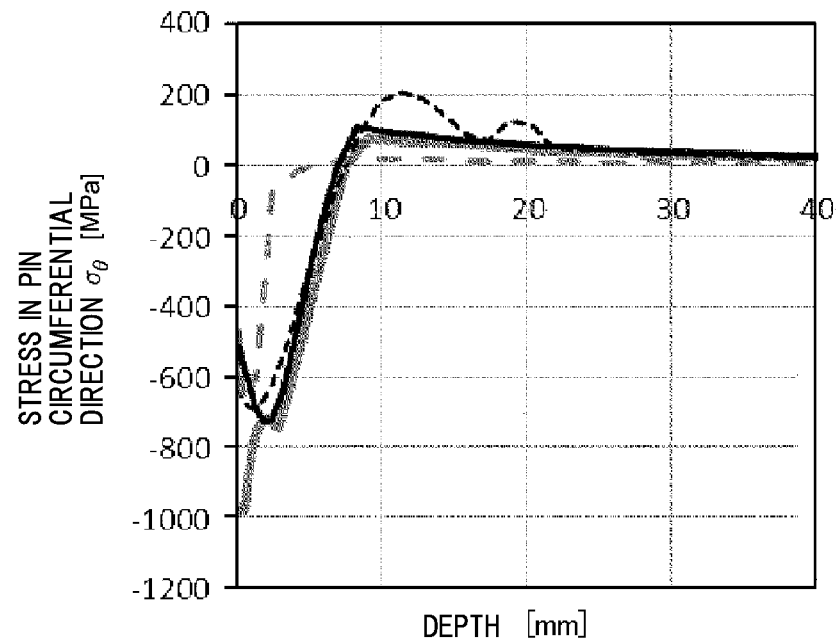
FIG. 12B is a graph illustrating estimation results of residual stress in a pin circumferential direction in Test 1.
Figure 12C:
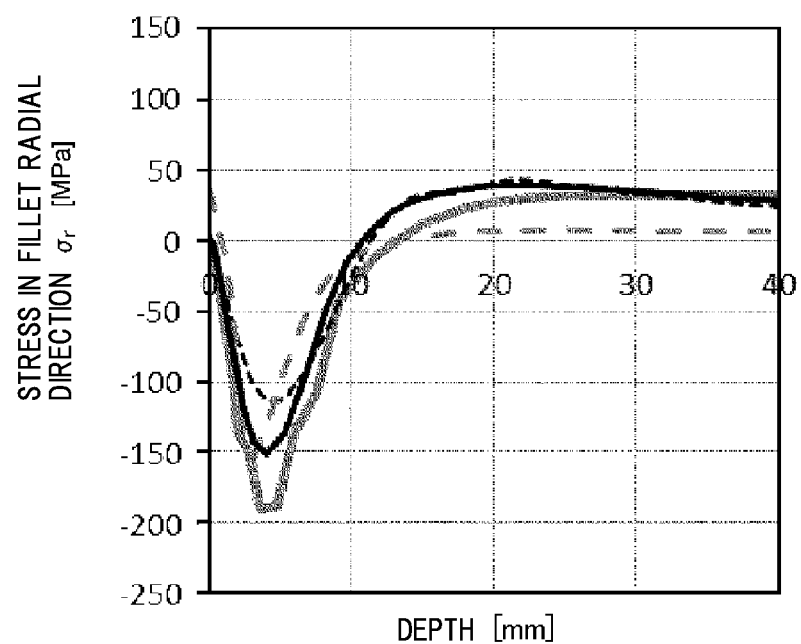
FIG. 12C is a graph illustrating estimation results of residual stress in a fillet radial direction in Test 1.

FIGS. 12A to 12C are graphs showing the results of Test 1. FIG. 12A is a graph illustrating estimation results of residual stress in a fillet circumferential direction, FIG. 12B is a graph illustrating estimation results of residual stress in a pin circumferential direction, and FIG. 12C is a graph illustrating estimation results of residual stress in a fillet radial direction. In FIGS. 12A to 12C, a vertical axis shows the magnitude of the residual stress, and a horizontal axis shows the depth from the surface. Further, in each graph, the gray solid line shows the correct answer value, the black dashed line shows the results of numerical experiment by comparative method 1, the gray dashed line shows the results of numerical experiment by comparative method 2, and the black solid line shows the results of numerical experiment by the proposed method.

The proposed method has obtained results that are very close to the correct answer value. On the other hand, the estimation precision of the residual stress in comparative method 1 and comparative method 2 is lower than that in the proposed method. In this way, it is possible to improve the estimation precision of the residual stress by setting the position and size of the analysis range using the analysis results of the theoretical analysis process.

(2) Test 2

Figure 13A:
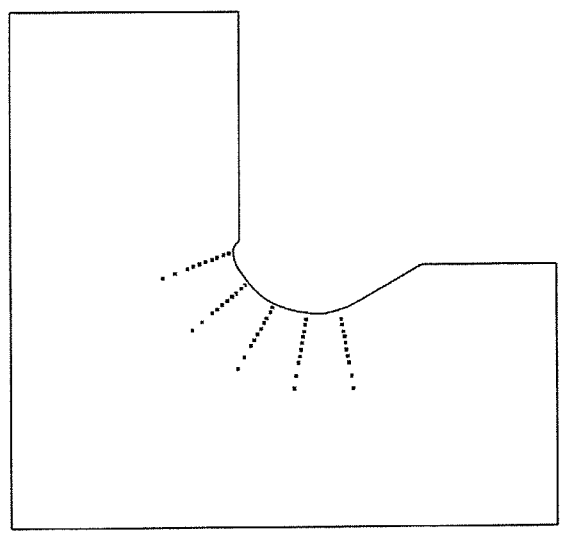
FIG. 13A is a view illustrating a measurement point in a proposed method.
Figure 13B:
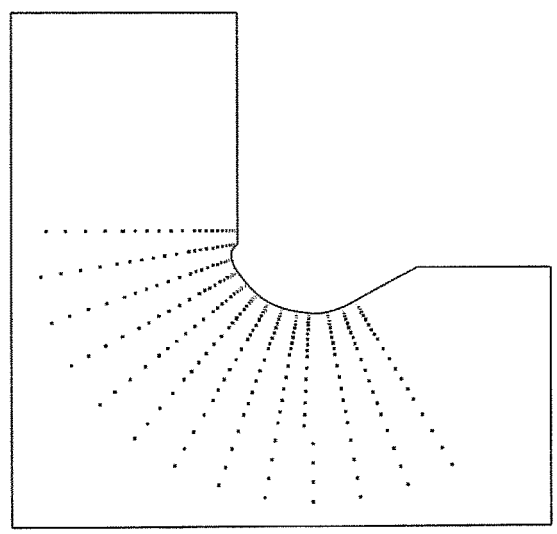
FIG. 13B is a view illustrating a measurement point in a comparative method 3.

In the proposed method, the measurement point was set in the strain generating region shown in the analysis results by the theoretical analysis process. For the case where there are more measurement points than the proposed method (hereinafter referred to as "comparative method 3"), the residual stress was estimated and compared with the results of the proposed method. FIG. 13A is a view illustrating a measurement point in a proposed method, and FIG. 13B is a view illustrating a measurement point in comparative method 3. In the drawings, the measurement point is indicated by black squares.

Figure 14A:
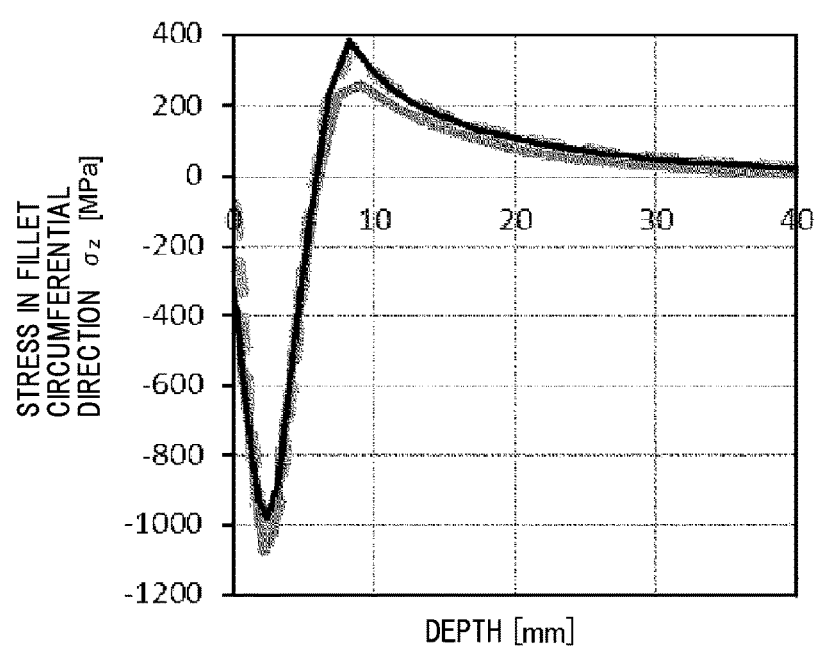
FIG. 14A is a graph illustrating estimation results of residual stress in the fillet circumferential direction in Test 2.
Figure 14B:
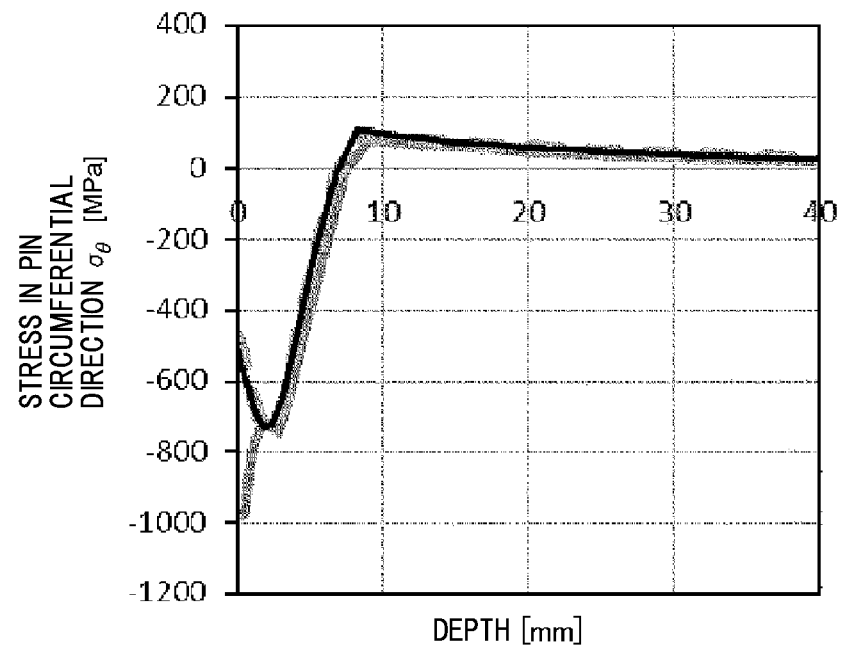
FIG. 14B is a graph illustrating estimation results of residual stress in the pin circumferential direction in Test 2.
Figure 14C:
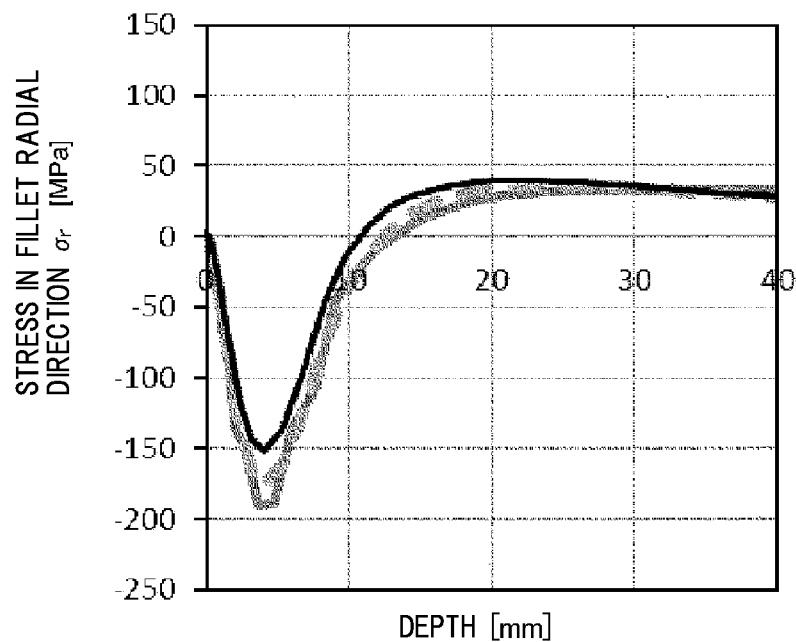
FIG. 14C is a graph illustrating estimation results of residual stress in the fillet radial direction in Test 2.

FIGS. 14A to 14C are graphs showing the results of Test 2. FIG. 14A is a graph illustrating estimation results of residual stress in a fillet circumferential direction, FIG. 14B is a graph illustrating estimation results of residual stress in a pin circumferential direction, and FIG. 14C is a graph illustrating estimation results of residual stress in a fillet radial direction. In FIGS. 14A to 14C, a vertical axis shows the magnitude of the residual stress, and a horizontal axis shows the depth from the surface. Further, in each graph, the gray solid line shows the correct answer value, the dashed line shows the results of numerical experiment by comparative method, and the black solid line shows the results of numerical experiment by the proposed method.

Both the proposed method and comparative method 3 have obtained results that are very close to the correct answer value. When measuring the inherent strain, it is necessary to collect the cut piece. Therefore, as the number of measurement points increases, it is effective for estimation precision, but operation cost becomes enormous. In the proposed method, it can be found that the estimation precision equivalent to that of comparative method 3 is secured while reducing the number of measurement points.

INDUSTRIAL APPLICABILITY

The residual stress estimation method and the residual stress estimation device of the present invention are useful as a residual stress estimation method and a residual stress estimation device for estimating the residual stress of a structure based on an inherent strain method.

The present application is based on Japanese Patent Application (Patent Application No. 2015-043083) filed on Mar. 5, 2015, the contents of which are incorporated herein by reference.

DESCRIPTION OF REFERENCE NUMERALS AND SIGNS

1: residual stress estimation device
10: computer
12: input unit
13: display unit
110: residual stress estimation program
111: CPU
115: hard disk
116: input/output interface
117: image output interface
200: crank shaft (structure)

The invention claimed is:

1. A residual stress estimation method based on inherent strain, comprising steps of:

analyzing strain generated in a structure and displaying analysis results, without using a measured value of the structure;

acquiring conditions concerning an analysis range, which is set based on the analysis results, for estimating residual stress;

acquiring the measured value for the residual stress of the structure; and estimating distribution of inherent strain in the analysis range using the measured value, based on the acquired conditions concerning the analysis range, to approximate the inherent strain of the structure in the analysis range.

2. The residual stress estimation method according to claim 1, wherein the step of acquiring conditions concerning the analysis range includes acquiring a position and a size of the analysis range as the conditions concerning the analysis range, and the step of estimating the distribution of the inherent strain includes estimating the distribution of the inherent strain in the analysis range specified by the acquired position and size.

3. The residual stress estimation method according to claim 2, wherein the step of acquiring the measured value includes acquiring elastic strain and residual stress measured at the measurement point in the analysis range specified by the acquired position and size as the measured value.

4. The residual stress estimation method according to claim 1, wherein the step of acquiring conditions concerning the analysis range includes acquiring information defining a plurality of divided regions that divide the analysis range as the conditions concerning the analysis range, and the step of estimating the distribution of the inherent strain includes determining a parameter of a distribution function to approximate the distribution function, which is a set of a plurality of piecewise functions defined for each of the plurality of divided regions defined by the acquired information, to the inherent strain distribution of the analysis range based on the measured value.

5. The residual stress estimation method according to claim 4, wherein the step of estimating the distribution of inherent strain includes determining the parameter of the distribution function so that each piecewise function is made continuous at a boundary of each divided region.

6. The residual stress estimation method according to claim 4, wherein the step of estimating the distribution of inherent strain includes determining the parameter of the distribution function based on spline interpolation so that a gradient of each piecewise function is made continuous at a boundary of each divided region.

7. The residual stress estimation method according to claim 1, wherein the step of displaying the analysis results includes performing elasto-plastic analysis on a three-dimensional model simulating the structure by a finite element method.

8. The residual stress estimation method according to claim 1, wherein the step of displaying the analysis results includes analyzing stress generated by processing of the structure based on Hertz contact theory.

9. A residual stress estimation device comprising:

an analysis unit for analyzing strain generated in a structure, without using a measured value of the structure;

a display unit for displaying analysis results by the analysis unit;

an input unit for receiving an input of conditions concerning an analysis range, which is set based on the analysis results, for estimating residual stress and a measured value for the residual stress of the structure;

an estimation unit for estimating distribution of inherent strain in the analysis range using the measured value, based on the conditions concerning the analysis range received by the input unit, to approximate the inherent strain of the structure in the analysis range; and a display unit for displaying the estimation results of the residual stress based on the distribution of the inherent strain estimated by the estimation unit.

\* \* \* \* \*